US010441952B2

(12) United States Patent
Rostaing et al.

(10) Patent No.: US 10,441,952 B2
(45) Date of Patent: Oct. 15, 2019

(54) DEVICE FOR PREPARING AND/OR TREATING A BIOLOGICAL SAMPLE

(75) Inventors: Hervé Rostaing, Le Versoud (FR); Laurent Drazek, Grenoble (FR)

(73) Assignee: bioMerieux, S.A., Marcy l'Etoile (FR)

( * ) Notice: Subject to any disclaimer, the term of this patent is extended or adjusted under 35 U.S.C. 154(b) by 1280 days.

(21) Appl. No.: 13/643,031

(22) PCT Filed: Apr. 21, 2011

(86) PCT No.: PCT/FR2011/050925
§ 371 (c)(1),
(2), (4) Date: Oct. 23, 2012

(87) PCT Pub. No.: WO2011/131914
PCT Pub. Date: Oct. 27, 2011

(65) Prior Publication Data
US 2013/0040406 A1    Feb. 14, 2013

(30) Foreign Application Priority Data

Apr. 23, 2010    (FR) ...................................... 10 53093

(51) Int. Cl.
*B01L 3/00* (2006.01)
*B01L 7/00* (2006.01)
*G01N 35/00* (2006.01)

(52) U.S. Cl.
CPC ... *B01L 3/502738* (2013.01); *B01L 3/502715* (2013.01); *B01L 3/502761* (2013.01); *B01L 7/52* (2013.01); *B01L 2200/0621* (2013.01); *B01L 2200/0631* (2013.01); *B01L 2200/0668* (2013.01); *B01L 2300/045* (2013.01); *B01L 2300/087* (2013.01); *B01L 2300/18* (2013.01); *B01L 2400/0487* (2013.01); *B01L 2400/065* (2013.01); *G01N 2035/00158* (2013.01)

(58) Field of Classification Search
CPC ................... B01J 19/0046; B01J 2219/00596
USPC .......................................... 436/180; 422/603
See application file for complete search history.

(56) References Cited

U.S. PATENT DOCUMENTS 6,440,725 B1    8/2002  Pourahmadi et al.
6,485,690 B1 *  11/2002  Pfost ................... B01J 19/0046
                                              422/552

(Continued)

FOREIGN PATENT DOCUMENTS

EP            0389063         8/1997

*Primary Examiner* — Natalia Levkovich

(57) ABSTRACT

The present invention relates to a device for preparation and/or treatment of a biological sample comprising a set of storage chambers and/or reaction chambers intended for receiving a fluid, the chambers being separated by walls so as to constitute a set of adjacent chambers. It also relates to an analysis apparatus capable of using such a device and also a method of using this device.

The device comprises a base and a drawer comprising the set of adjacent chambers, the drawer being movable relative to the base, the drawer comprising a contact surface on which emerge first means for placing in fluidic communication linked to the volume of at least one chamber, the contact surface of the drawer being intended to be positioned facing a contact surface of the base comprising at least one position at which there are arranged second fluidic communication means linked to detection means.

The invention has a preferred application in the field of medical diagnosis.

15 Claims, 6 Drawing Sheets

(56) References Cited

U.S. PATENT DOCUMENTS

| | | |
|---|---|---|
| 6,734,684 B2 | 5/2004 | Golo |
| 6,878,540 B2 | 4/2005 | Pourahmadi et al. |
| 6,881,541 B2 | 4/2005 | Petersen et al. |
| 6,964,862 B2 | 11/2005 | Chen |
| 2003/0175165 A1 | 9/2003 | Liu |
| 2004/0184967 A1 | 9/2004 | Parng et al. |
| 2006/0078931 A1* | 4/2006 | Oh .................... B01L 3/502715 435/6.11 |
| 2008/0038714 A1 | 2/2008 | Gao et al. |
| 2011/0200486 A1 | 8/2011 | Beumer et al. |

\* cited by examiner

B - B

C - C

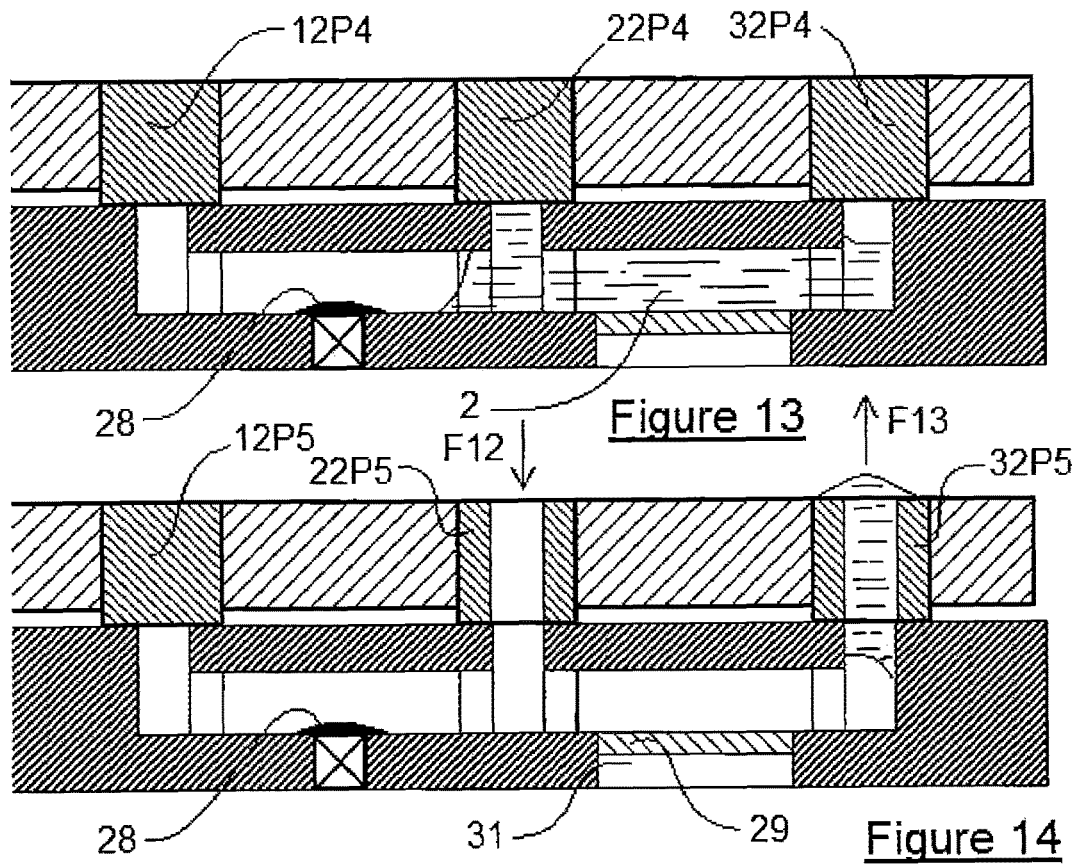
Figure 13
Figure 14
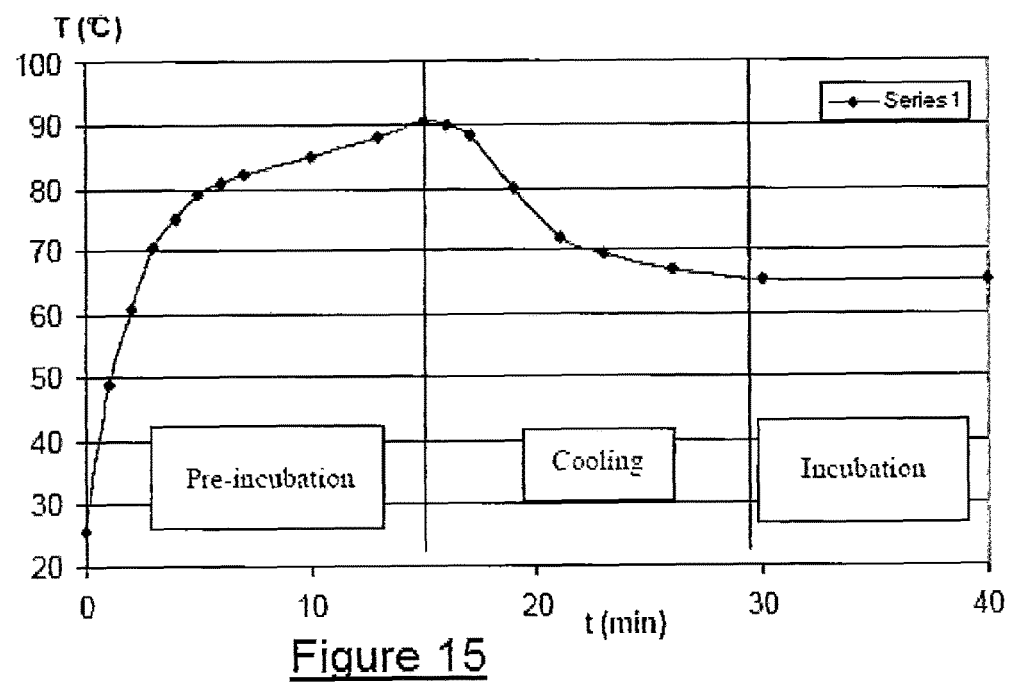
Figure 15

DEVICE FOR PREPARING AND/OR TREATING A BIOLOGICAL SAMPLE

CROSS REFERENCE TO RELATED APPLICATIONS

This application is the national stage application under 35 USC § 371 of International Application No. PCT/FR2011/050925, filed Apr. 21, 2011, which claims the benefit of French Patent Application No. 1053093, filed Apr. 23, 2010, the disclosures of which are hereby incorporated by reference.

The present invention relates to a device for preparation and/or treatment of a biological sample.

Such a device is particularly intended to be used within the framework of the automation of biological protocols, particularly complex biological protocols.

By way of non-limiting example, such a device can be applied to the detection of pathogens or molecules, nucleic acids or proteins of a pathogen.

Such a biological protocol must preferably be performed in a low-cost consumable device, linked to the detection module, and which is changed between each test. This consumable can be inserted into a treatment apparatus containing costly components, for example mechanical or optical components.

Different techniques are used to automate complex biological protocols, such as logic test protocols, also called immunoassays, from a sample of a few milliliters. In all cases, the presence of several reagents makes necessary the existence of different storage chambers and at least one reaction chamber. Means which allow the displacement of the fluids are also necessary.

A first known device, which is used in particular by the company Genpoint and which implements a preparation robot marketed by the company Tecan, comprises means for displacing a pipette in three dimensions and a plate presenting a plurality of wells, the wells containing either a reagent or a sample.

The pipette is displaced above the plate so as to be positioned in a well in order to sample a quantity of reagent, then positioned in the well containing the sample in order to deliver the quantity of reagent into this well, and does this successively for each reagent.

Additional means necessary to the progress of the reactions, in particular heating means or magnetic capture means, can be arranged under the plate.

Such a device has the disadvantage of using precision mechanical means to displace the pipette which have a complex structure and are difficult to transport.

To avoid the contaminations between tests, it has therefore been envisaged to perform individual tests in single-use hermetic devices.

Thus the documents U.S. Pat. Nos. 6,878,540, 6,440,725 and 6,881,541 describe devices including a single-use cartridge comprising a set of chambers or reservoirs intended to receive in particular a sample, washing fluids, elution fluids, reagents, the chambers or reservoirs being linked by a set of channels. These devices also comprise a microfluidic chip. The movement of the fluids between the different chambers and reservoirs is effected by means of the set of channels under the effect of pumps and flow control means of valve type or fluid diode type. One of the uses of these devices is to perform the treatment of a fluid sample to extract and amplify nucleic acids, particularly by PCR.

For its part, the document U.S. Pat. No. 6,734,684 also describes a single-use cartridge comprising a set of chambers and reservoirs. In the case of this document, a single treatment chamber is used which can be placed in fluidic communication with other chambers or reservoirs selectively by means of channels provided in a rotary mechanism.

These solutions effectively make it possible to reduce the contaminations, but involve the deployment of a structure of fluidic communication between the chambers and of displacement which remains complex.

The document U.S. Pat. No. 6,964,862 describes a device comprising a single-use element having chambers separated by walls which allow a fluidic communication above a determined pressure. Each chamber is filled with a specific fluid before closure. Putting the fluids contained in two neighbouring chambers into communication is performed by mechanical pressure on one of the two chambers, which causes an opening to appear in the separating wall.

This latter device makes it possible to simplify the production of the communication between the chambers, and also makes it possible to limit the contamination between tests.

Given the miniaturisation of the above-mentioned devices, the quantities of liquids used are of smaller and smaller volumes. These quantities become so low that the use of single-use containers with integrated reagents is made difficult. Indeed, for cost reasons, the materials used to form the chambers or the reservoirs are produced from basic and cheap plastic materials, such as polyolefins. These materials do not make it possible to obtain a durable tightness and present poor barrier properties without suitable treatment. Thus, a diffusion can take place through the walls. In particular there result changes in the concentration of the reagents due to the evaporation of the solvent. Such an evaporation can be ignored in the case of quantities of several hundred µl, but cannot be ignored in the case of reagent volumes lower than 50 µl, above all during high incubations and over substantial times (several hours).

This indicates that it is advisable to place the reagents in the device only just before they are used.

Given the miniaturisation of the devices mentioned hereabove, the size of the devices themselves is reduced. It can be estimated that the size limit for allowing easy handling is in the region of 10 mm. An operator cannot assemble or handle elements of this size given the time which he would require for each operation and the risk of losing parts of the device. It is more practical to use sets of disposable devices comprising up to several hundred devices. An automatic apparatus will deal with the manipulation of the single-use disposable devices.

It should finally be noted that the devices are assembled from several elements coming from different manufacturers. It is therefore advisable that the structure of these devices be suitable for an assembly which must be automated given that the prevailing tolerances are in the region of ten µm.

It is therefore desirable to provide a device of small size which can easily be filled and used by an automatic apparatus. This apparatus must also be inexpensive, and easy to manufacture, whilst allowing satisfactory performance.

The Applicant has already filed a French patent application on 5 Nov. 2008, under filing No. 08/06169, which aims to resolve all or part of the disadvantages mentioned above.

To this end, the subject of this application is a device for preparation, treatment and/or analysis of a biological sample comprising a base and a drawer which is movable in translation relative to the base comprising a set of storage and/or reaction chambers intended for receiving a fluid, the chambers being separated by walls so as to constitute a set of adjacent chambers, the drawer further comprising a contact surface on which emerge the first means for placing in fluidic communication linked to the internal volume of the chambers, the contact surface of the drawer being positioned facing a contact surface of the base comprising at least one position at which there are arranged second fluidic communication means linked to detection means.

Despite the fact that this invention addresses the above-mentioned disadvantages, it poses other disadvantages which are as follows:

It does not make it possible to perform complex methods, such as those requiring a pretreatment of the sample of interest. This is the case, for example, in molecular biology in which it is important to be able to lyse the cells in order to make the nucleic acids which they contain accessible to other treatment (detection amplification in particular).

The link between the drawer, referred to as the mobile part, and the base, referred to as the fixed part, is effected by means of at least two seals which are particularly sophisticated since they are made of a different material to the base or the drawer and positioned concentrically relative to the opening for the passage of the sample.

Finally, if there is liquid-tightness, they are however not gas-tight.

The present invention has the aim of resolving all or part of the above-mentioned disadvantages.

To this end, the subject of the present invention is a device for preparation, treatment and/or analysis of at least one liquid, preferably a biological sample, comprising:

a reaction support, having a set of at least two chambers, this set comprising:
  at least one central channel comprising:
    on the one hand, an internal pipe which allows the chambers to be linked to one another so as to constitute a set of adjacent chambers, and
    on the other hand, an external pipe which makes it possible to link the internal pipe which emerges to the exterior, and
  at least one emerging channel per chamber, situated substantially upstream and downstream of each chamber, called the upstream channel and downstream channel,
a drawer, which is movable in translation relative to the reaction support, between at least two positions, and having, for each position, at least three control means capable of cooperating to close and/or to open the emerging channels, in order to bring the internal volume of the chambers into (open control means) or out of (closed control means) fluidic communication with the exterior of the device.

According to an embodiment of the device, the reaction support consists of two parts:
  a base having means which allow the drawer to move in translation, and
  a reaction element comprising the chambers and channels.

According to another embodiment of the device, the reaction element consists of two parts:
  a reaction chip, and
  a reading window which makes detection possible at the chip.

According to yet another embodiment of the device, each control means of the drawer includes a sealing means capable of cooperating with the contact surface of the reaction support at each translatory position.

Still according to another embodiment of the device, all of the chambers, channels and control means in fluidic relationship are aligned relative to one another for each translation position.

According to yet another embodiment of the device, and in order to allow the separation and incubation of a liquid biological sample, the device possesses:
  two adjacent chambers:
    a first transfer chamber, and
    a second reaction chamber,
  and three emerging channels:
    a first channel upstream of the transfer chamber,
    a second channel downstream of the first transfer chamber and upstream of the second reaction chamber, at the channel linking the two chambers, and
    a third channel downstream of said reaction chamber,
  cooperating with several lines of three control means borne by the drawer:
    a first means facing the first channel,
    a second means facing the second channel,
    a third means facing the third channel.

In accordance with an alternative embodiment emerging from the preceding one, at least one of the chambers includes a reading area.

Whatever the embodiment or the alternative embodiment of the device, the drawer includes in at least one position a magnet capable of acting on at least one of the chambers to allow the separation of magnetic particles present in the liquid.

According to another embodiment of the device, the base includes in at least one position a magnet capable of acting on at least one of the chambers to allow the separation of magnetic particles present in the liquid.

The present invention also relates to an analysis apparatus capable of using a device such as described above, which includes:
  driving means allowing the relative movement of the drawer relative to the reaction support,
  means for transferring (addition, withdrawal or movement within the device) all or part of a liquid, such as a biological sample to be treated or liquid(s) (washing liquid, elution liquid) necessary for the implementation of the following method and combination of these, and
  control means capable of allowing the good operation and the good synchronisation of the driving means, of the transfer means.

According to an embodiment of the apparatus when it is intended to allow the incubation of the biological sample further comprising heating means which themselves function under the control of the control means.

According to another embodiment of the apparatus, it comprises, at the transfer means, a pipette tip or a needle capable of cooperating with each of the control means at each position.

The invention also proposes a method of use of a device, described above, or implementing an apparatus, such as disclosed below, wherein:
  a liquid is introduced into the first chamber by injecting it into the first control means, by opening the second control means and by closing the third control means, and/or
  a liquid is introduced into the first chamber by injecting it into the second control means, by opening the first control means and by closing the third control means, and/or a liquid is introduced into the second chamber by injecting it into the second control means, by opening the third control means and by closing the first control means, and/or a liquid is introduced into the second chamber by injecting it into the third control means, by opening the second control means and by closing the first control means, and/or a liquid is introduced into the first and second chambers by injecting it into the first control means, by opening the third control means and by closing the second control means, and/or a liquid is introduced into the first and second chambers by injecting it into the third control means, by opening the first control means and by closing the second control means, and/or a liquid present in the first chamber is purged by injecting or by aspirating a fluid into the first control means, by opening the second control means and by closing the third control means, and/or a liquid present in the first chamber is purged by injecting or by aspirating a fluid into the second control means, by opening the first control means and by closing the third control means, and/or a liquid present in the first chamber is purged by injecting or by aspirating a fluid into the third control means, by opening the first control means and by closing the second control means, and/or a liquid present in the first chamber is purged by injecting a fluid into the first control means, by opening the third control means and by closing the second control means, and/or a liquid present in the second chamber is purged by injecting or by aspirating a fluid into the second control means, by opening the third control means and by closing the first control means, and/or a liquid present in the second chamber is purged by injecting or by aspirating a fluid into the third control means, by opening the second control means and by closing the first control means, and/or a liquid present in the second chamber is purged by injecting or by aspirating a fluid into the third control means, by opening the first control means and by closing the second control means, and/or a liquid present in the second chamber is purged by injecting or by aspirating a fluid into the first control means, by opening the third control means and by closing the second control means, and/or a liquid present in the first and second chambers is purged by injecting or by aspirating a fluid into the first control means, by opening the third control means and by closing the second control means, and/or a liquid present in the first and second chambers is purged by injecting or by aspirating a fluid into the third control means, by opening the first control means and by closing the second control means, and/or a liquid present in the first and second chambers is purged by injecting or by aspirating a fluid into the second control means, by opening the first and third control means, and/or a liquid is incubated in the first chamber by closing the first and second control means and by applying a source of heat to said first chamber, and/or a liquid is incubated in the second chamber by closing the second and third control means and by applying a source of heat to said second chamber, and/or a liquid is incubated in the first and second chambers by closing the control means and by applying a source of heat to said first and second chambers, and/or a precise volume of a liquid is sampled at the first chamber, firstly, by opening the first and second control means, by closing the third control means and by pushing, with the aid of a fluid, the liquid, via the first control means, until it overflows at the second means, and finally by translating the drawer relative to the support, and/or a precise volume of a liquid is sampled at the first chamber, firstly, by opening the first and second control means, by closing the third control means and by pushing, with the aid of a fluid, the liquid, via the second control means, until it overflows at the first control means, and finally by translating the drawer relative to the support, and/or a precise volume of a liquid is sampled at the second chamber, firstly, by opening the second and third control means, by closing the first control means and by pushing, with the aid of a fluid, the liquid, via the second control means, until it overflows at the third control means, and finally by translating the drawer relative to the support, and/or a precise volume of a liquid is sampled at the second chamber, firstly, by opening the second and third control means, by closing the first control means and by pushing, with the aid of a fluid, the liquid, via the third control means, until it overflows at the second control means, and finally by translating the drawer relative to the support, and/or a precise volume of a liquid is sampled at the first and second chambers, firstly, by opening the first and third control means, by closing the second control means and by pushing, with the aid of a fluid, the liquid, via the first control means, until it overflows at the third control means, and finally by translating the drawer relative to the support, and/or a precise volume of a liquid is sampled at the first and second chambers, firstly, by opening the first and third control means, by closing the second control means and by pushing, with the aid of a fluid, the liquid, via the third control means, until it overflows at the first control means, and finally by translating the drawer relative to the support, and/or a movement of a liquid back and forth is carried out at the first chamber, firstly by injecting it into the first control means, by opening the second control means and by closing the third control means, then, by translating the drawer relative to the support into a position which closes the second control means, and finally by at least once pushing, with the aid of a fluid, through the first control means, the liquid present in the first chamber towards or into the second chamber by compressing the air trapped in said second chamber and/or a movement of a liquid back and forth is carried out at the first chamber, firstly by injecting it into the second control means, by opening the first control means and by closing the third control means, then, by translating the drawer relative to the support into a position which closes the second control means, and finally by at least once pushing, with the aid of a fluid, through the first control means, the liquid present in the first chamber towards or into the second chamber by compressing the air trapped in said second chamber and/or a movement of a liquid back and forth is carried out at the second chamber, firstly by injecting it into the second control means, by opening the third control means and by closing the first control means, then, by translating the drawer relative to the support into a position which closes the second control means, and finally by at least once pushing, with the aid of a fluid, through the third control means, the liquid present in the second chamber towards or into the first chamber by compressing the air trapped in said first chamber and/or a movement of a liquid back and forth is carried out at the second chamber, firstly by injecting it into the third control means, by opening the second control means and by closing the first control means, then, by translating the drawer relative to the support into a position which closes the second control means, and finally by at least once pushing, with the aid of a fluid, through the third control means, the liquid present in the second chamber towards or into the first chamber by compressing the air trapped in said first chamber.

According to an embodiment of the preceding method, when a liquid present in one or both of the first and second chambers is purged by injecting a fluid through one of the control means and by evacuating it via one of the other control means, this other control means is linked to a reservoir for collecting surplus liquids via a channel.

The present invention finally relates to a method for separation and incubation within a device, such as described above, or implementing an apparatus, according to the characteristics set out above, comprising the following steps:

a liquid, containing nucleic acids of interest captured on magnetic beads, is introduced into the first chamber by injecting it into the first control means, while opening the second control means and closing the third control means, the surplus liquid exits into a collection reservoir via a channel, in this position a magnet is present in the vicinity of, preferably under, said first chamber, which makes it possible to capture the magnetic particles and the nucleic acids, then the liquid present in the first chamber is purged by injecting air into the first control means, whilst keeping the third control means closed, and once again the residual liquid exits into the collection reservoir via the channel, the drawer is translated relative to the support into a position in which there is still a magnet in the vicinity of, preferably under, the first chamber, a precise volume of an elution liquid is sampled at the second chamber, the second and third control means being open and the first control means being closed, and the liquid is pushed, via the third control means, until it overflows at the second control means, the support is translated relative to the drawer into a position in which there is still a magnet in the vicinity of, preferably under, the first chamber, a movement of said elution liquid back and forth is carried out by pushing it and by releasing via the third control means at least once from the second chamber towards or into the first chamber by compression of the air trapped in said first chamber, the first and second control means being closed, the nucleic acids are released into the elution liquid, while being incubated between 35 and 50° C., preferably at substantially 40° C., the support is translated relative to the drawer, and this liquid is incubated by keeping the control means closed and by applying a second source of heat to said second chamber, which makes possible the hybridisation of the nucleic acids on the reaction chip whilst incubating between 40 and 80° C., preferably at substantially 65° C., the second chamber is washed and an optical reading of the hybridisation of the nucleic acids on said chip is carried out.

The invention will be better understood with the aid of the detailed description which is set out hereafter with regard to the attached figures, namely:

Figure 4:
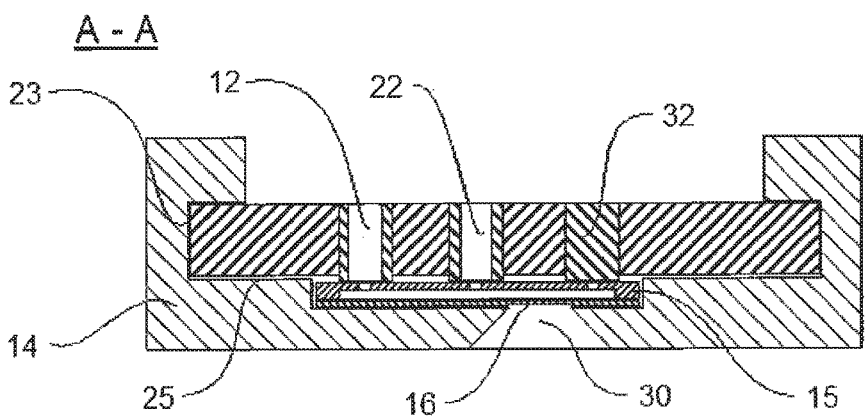
FIG. 4 is a sectional view along A-A in FIG. 1, at an enlarged scale relative to this FIG. 1.
Figure 8:
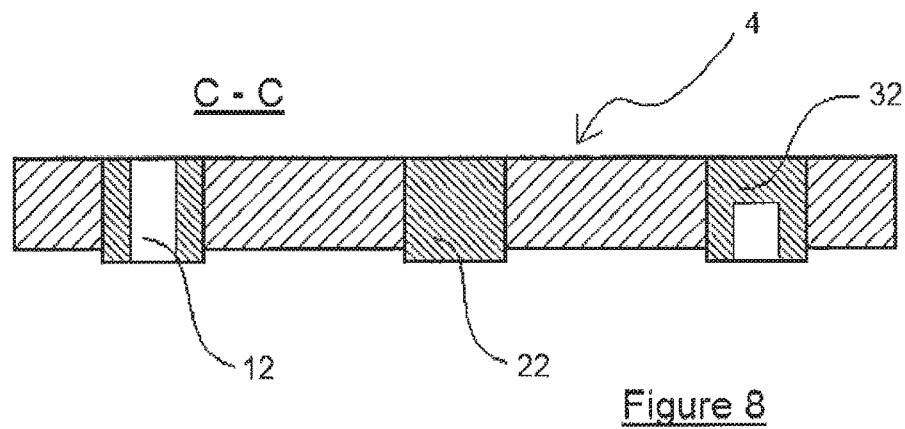
FIG. 8 is a sectional view along C-C of FIG. 7, at an enlarged scale relative to said FIG. 7.

a reaction chip, borne by a base, which is not shown in this figure, such as presented in FIG. 4, and a drawer according to FIG. 8, in a separation and incubation method, the device being configured relative to a first step of the method.

Figure 9:
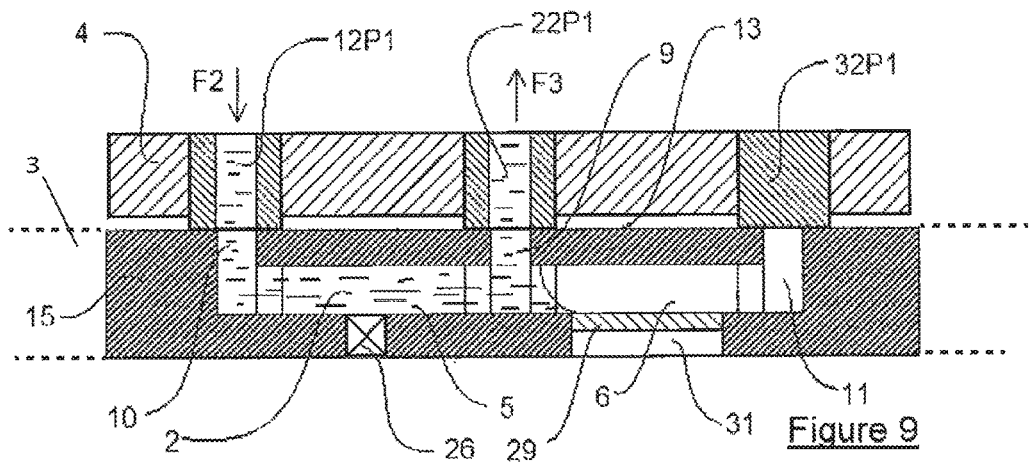
FIG. 9 is a sectional view of a device according to the invention, associating.
Figure 10:
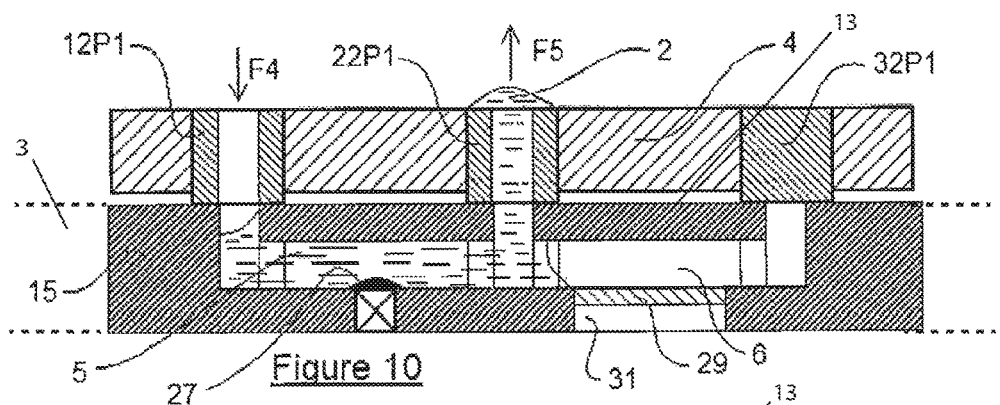

FIG. 10 is a sectional view identical to FIG. 9 of said device which is configured relative to a second step of the method.

Figure 11:
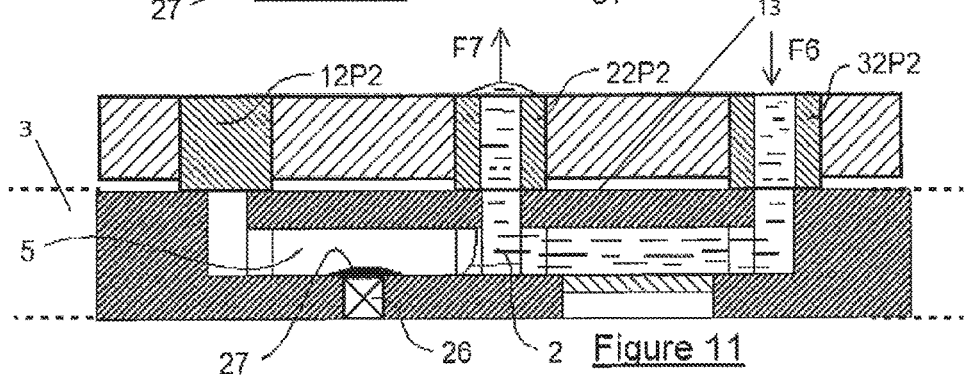

FIG. 11 is a sectional view identical to FIGS. 9 and 10 of said device which is configured in a relationship with a third step of the method.

Figure 12:
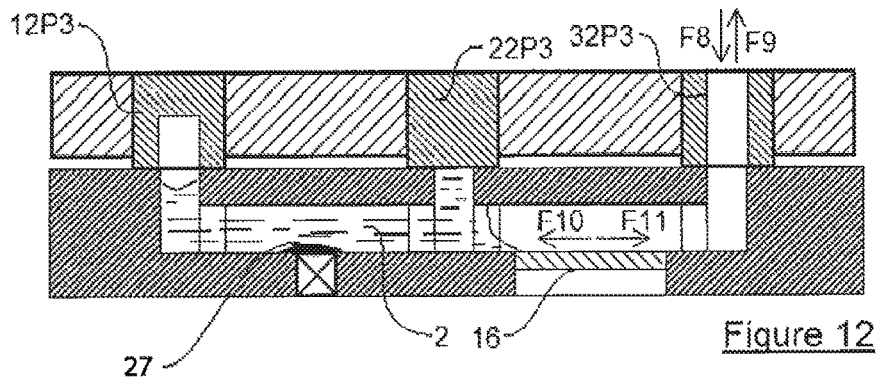

FIG. 12 is a sectional view identical to FIGS. 9 to 11 of said device which is configured relative to a fourth step of the method.

FIG. 13 is a sectional view identical to FIGS. 9 to 12 of the device which is configured relative to a fifth step of the method.

FIG. 14 is a sectional view identical to FIGS. 9 to 13 of said device which is configured relative to a sixth step of the method.

FIG. 15 is a depiction of the curve of the denaturation of the nucleic acids (in particular RNA strands) by heat at a temperature of 90° C. of the device according to the invention, before incubation at 65° C.

Figure 16:
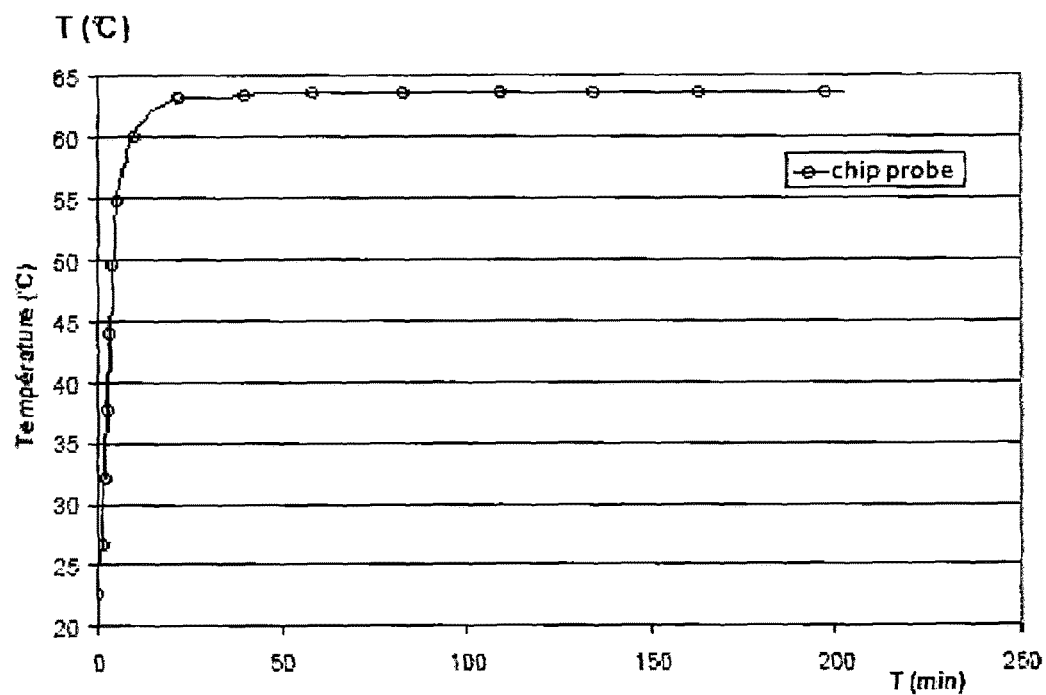

FIG. 16 is a depiction of the implementation of the warming-up of the same device but for 3 hours, still to demonstrate the temperature stability of our invention.

Figure 17:
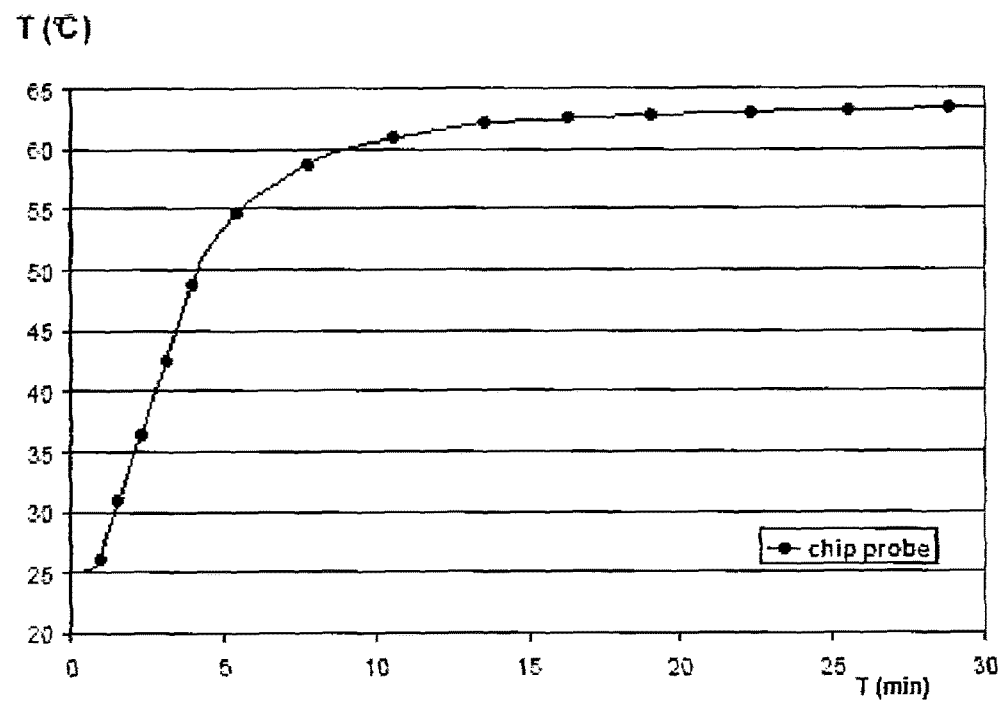

Finally FIG. 17 is a depiction of the warming-up of said device according to the invention for 20 minutes.

In the following detailed description of the figures defined above, the same elements or the elements which fulfil identical functions can retain the same references so as to simplify comprehension of the invention.

The present invention relates to a device 1 intended to allow the treatment of a biological sample 2. Such a device 1 is clearly shown, for example, in FIG. 1. This treatment device 1 includes, on the one hand, a reaction support 3 and, on the other hand, a drawer 4. In this FIG. 1, it is understood that the drawer 4 can slide in the support 3 in the direction of arrow F1. Of course, a reverse movement can also be envisaged, or even a joint movement of the support 3 and drawer 4. To allow this movement in the direction F1, the support 3 consists of three parts, which do not bear references, a lower part and two upper parts facing one another. Each of the two upper parts constitutes with the lower part a shoulder which creates a slideway 23. The drawer 4 includes various pipes which make it possible to link the non-visible chambers in this figure, as will be explained better hereafter.

It is also recognised that the support 3 includes a certain number of elements on the upper face of its lower plate consisting particularly of grooves 25 which facilitate the sliding in the direction F1 and the contact between support 3 and drawer 4.

Figure 1:
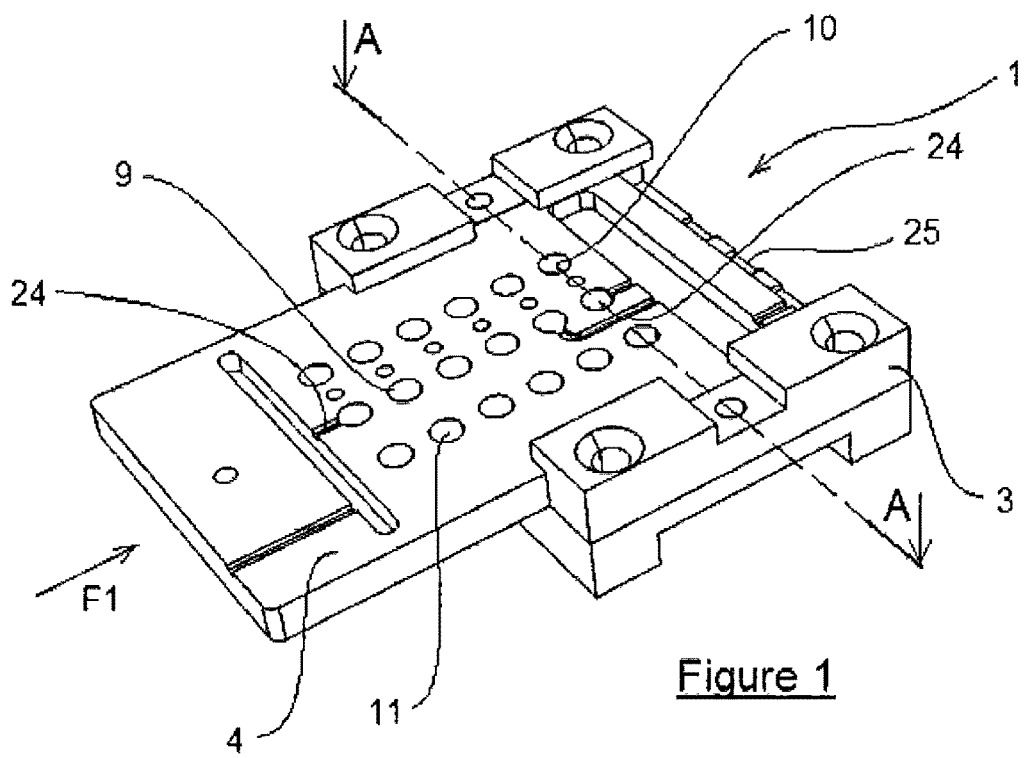
FIG. 1 is a perspective view of a first device according to the invention seen from above.
Figure 2:
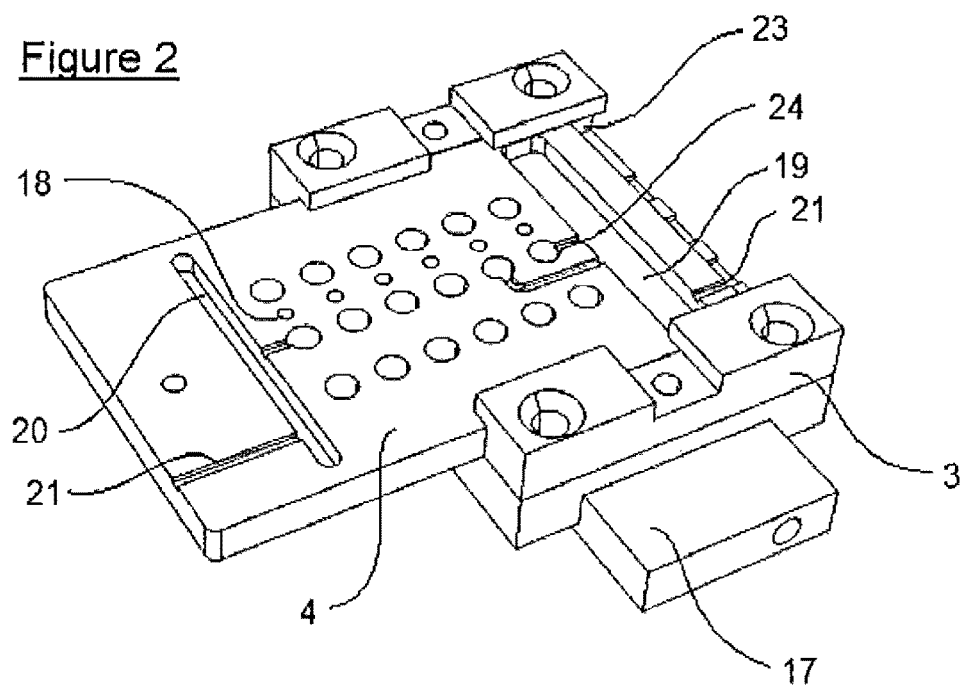
FIG. 2 is a view of the device identical to that of FIG. 1 but further including an incubator.

FIG. 2 is identical to FIG. 1, but an inserted element has been added to it. It is an incubator 17 which allows the device to incubate the biological sample 2 when this is present within the device 1. Furthermore, other elements are also referenced in this FIG. 2. In particular, there is the upstream reservoir 19 and the downstream reservoir 20 for collecting surplus liquids, from the vent 21 present between the reservoirs 19 and 20 and the exterior. There are therefore two vents, in this figure, one on the left and one on the right, each associated with one of the two reservoirs 19 and 20. Finally, FIG. 2 includes indexing holes 18 which are positioned between two channels, namely the upstream channel 10 and the downstream channel 11, which will be better defined hereafter.

Of course these indexing holes 18 could be positioned elsewhere on the card or be unnecessary due to the use of a stepper motor of which the step corresponds to the distance between two adjacent channels for example 10.

In another embodiment which will be better described hereafter, these indexing holes 18 can also be replaced by magnets which have a certain function within the framework of the method of using the device 1.

Figure 3:
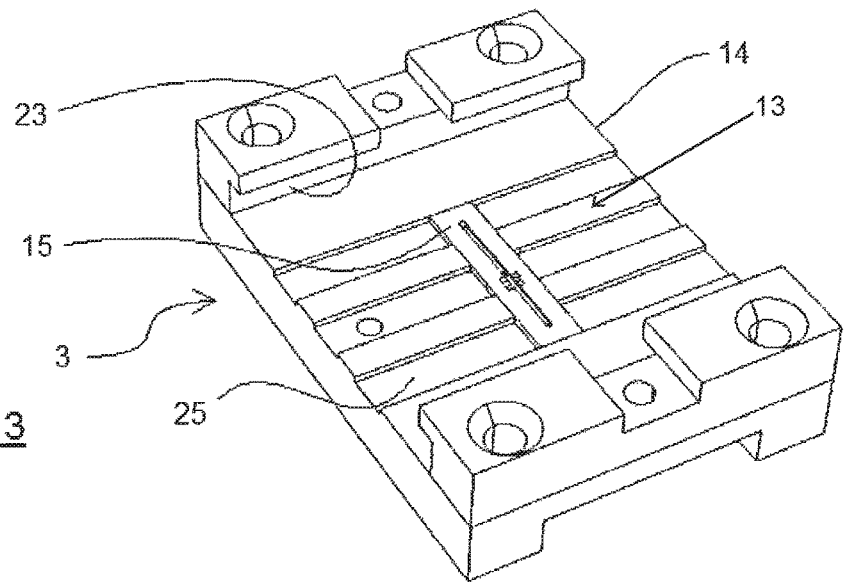
FIG. 3 is a partial view of the device of FIG. 1, wherein the drawer has been pulled out; there is therefore nothing more than the base of the device which bears an added microfluidic reaction chip which is present.

FIG. 3 presents just a part of the device 1, namely the reaction support 3. This embodiment offers the best view of the three-element structure of said support 3, namely the lower plate and the two upper elements, not referenced, which due to the shoulders constitute with this lower plate the two slideways 23. Note is also taken of the presence of an inserted element, called a reaction element or reaction chip 15, which is installed within the support 3 on the upper part of the lower plate thereof.

This chip 15 is advantageously fixed by gluing, or even simply snapped in or laid down, on the upper face 15 of the base 14 of the support 3.

The manufacture of the support 3 can be performed by plastic injection, in particular from a single material. Different materials can be used for the support 3 which must preferably present the following properties:
- a high degree of flatness, that is to say no excessive shrinkage or deformation during ejection of the piece from the mould,
- a smooth surface, and
- good mechanical strength to firmly hold the drawer 4 against the contact surface of the base.

The position of the injection point must be chosen so as to allow satisfactory flatness and filling. Furthermore, the design of the base must take into account the deformation under stress due to the mounting of the drawer 4. The support 3 can, for example, be made of polycarbonate (PC), polystyrene (PS), polymethyl methacrylate (PMMA), polyetherimide (PEI), polyethylene terephthalate (PET), polyethylene naphthlate (PEN), acrylonitrile-butadiene-styrene (ABS), styrene-acrylonitrile (SAN).

The drawer 4 is also an item made of injected plastic which can be produced in two different ways, with a single injection or a double injection of two different materials.

The single injection allows easier and less costly manufacture, and co-injection makes it possible to improve the robustness of the whole.

The drawer 4 manufactured from a single material can be produced from different polymers, such as in particular thermoplastic polymers or thermoplastic elastomers.

The drawer 4, which is not shown in the figures, is made from a single material, which of course makes it possible to simplify its manufacture.

According to an alternative embodiment of the drawer 4, shown in the figures, this 4 comprises two parts constituted by two distinct materials, the part which constitutes the body of said drawer comprising a material which is more rigid than that which constitutes the control means.

The base 14 of the support 3 is particularly smooth in order to allow the good translation in the direction F1 of the drawer 4. The presence is also noted, on this surface 13 of the support 3, of grooves 25 on said contact surface 13 which make possible the passage of the control means 12, 22 and 32.

FIG. 4 is a sectional depiction along A-A of FIG. 1. On grounds of simplicity, the reaction support 3 is one-piece in this embodiment. Furthermore, the reaction element 15 is an inserted element. This inserted element is therefore glued inside the support 3, but is nevertheless visible from the exterior via a reading window 30 which corresponds to a reading area 16 of the reaction element 15. The drawer 4 in this sectional view therefore includes three control means bearing the references, from left to right, 12, 22 and 32. These control means 12, 22 and 32 cooperate with the reaction chip 15.

In this regard, it is noted that the lower surface of the drawer 4 includes three protuberances extending downwards at the control means 12, 22 and 32. In fact, the control means 12, 22 and 32 correspond directly to the external pipes 9 and to the upstream channels 10 and 11 of the reaction chip 15, and can be moved in translation in the direction F1 at the grooves 25.

Figure 5:
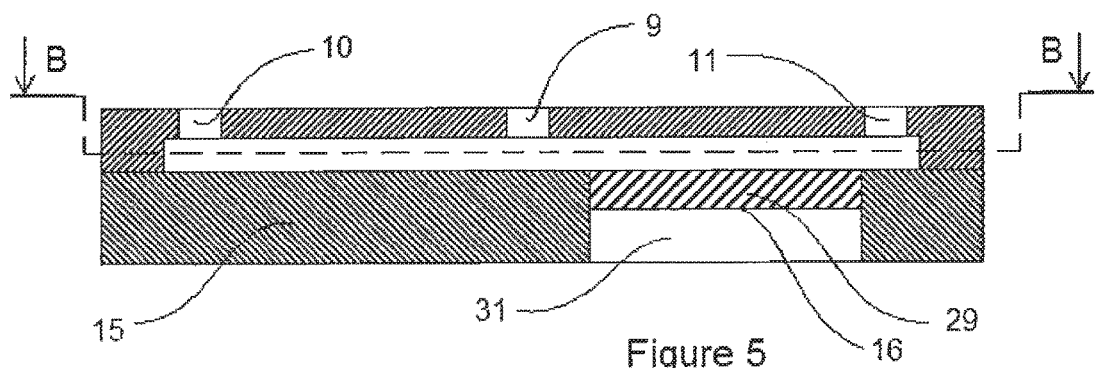
FIG. 5 is an enlarged view of a part of the section along A-A of FIG. 1, or of the reaction chip of FIG. 4 at an enlarged scale relative to these FIGS. 1 and 4.

This reaction chip 15 is for example well described in FIG. 5, which depicts a magnification of said chip 15 present in this FIG. 4. In this case, note is taken of the presence of three channels linking the inner cavity which is unreferenced in this figure towards the upper part of said chip 15. These are the external pipe 9, the upstream channel 10 and the downstream channel 11.

It should also be noted that the reading window 30, clearly shown in FIG. 4, corresponds to a reading window 31 of the element 15, as is clearly shown in FIG. 5.

Figure 6:
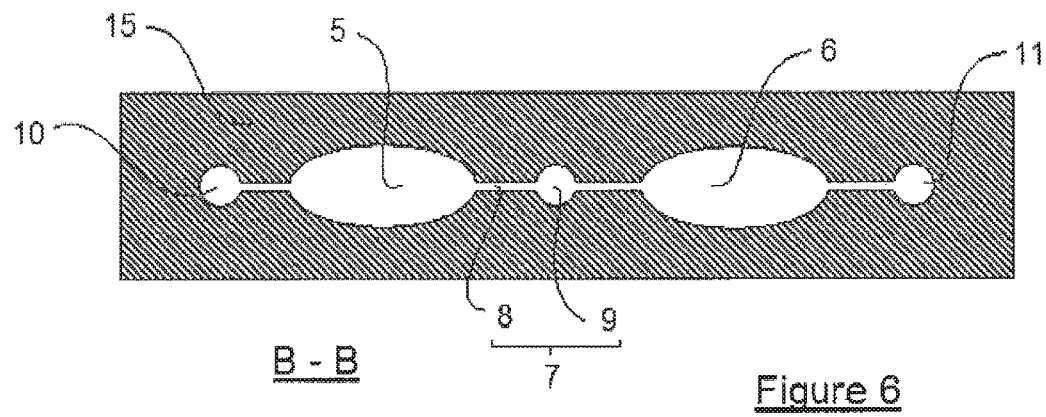
FIG. 6 is a sectional view along B-B of FIG. 5.

The structure of this chip 15 is better understood as shown in a sectional view along B-B of FIG. 5. In fact, in FIG. 6, the external pipe 9 makes it possible to link an internal pipe 8 which emerges to the exterior. This internal pipe 8 makes it possible to link two chambers 5, on the left, and 6, on the right. The chamber 5 also comprises on its left-hand side an upstream channel 10 which links said chamber 5 to the exterior. The chamber 6 likewise includes a downstream channel 11 which links said chamber 6 to the exterior. These are therefore those channels 9, 10 and 11 of the chip 15, and therefore of the support 3, which correspond to the control means 12, 22 and 32 of the drawer 4. It should be noted that the set of internal 8 and external 9 pipes situated between the two chambers 5 and 6 of the reaction element 15 constitute the central channel 7, as is clearly shown in FIG. 6.

At the reading window 31 of the element 15, the reaction chip 29 is present which makes it possible to have a contact, albeit only optical, with the interior of the reaction chamber 6. This reaction chip 29 therefore includes a reading area 16.

Figure 7:
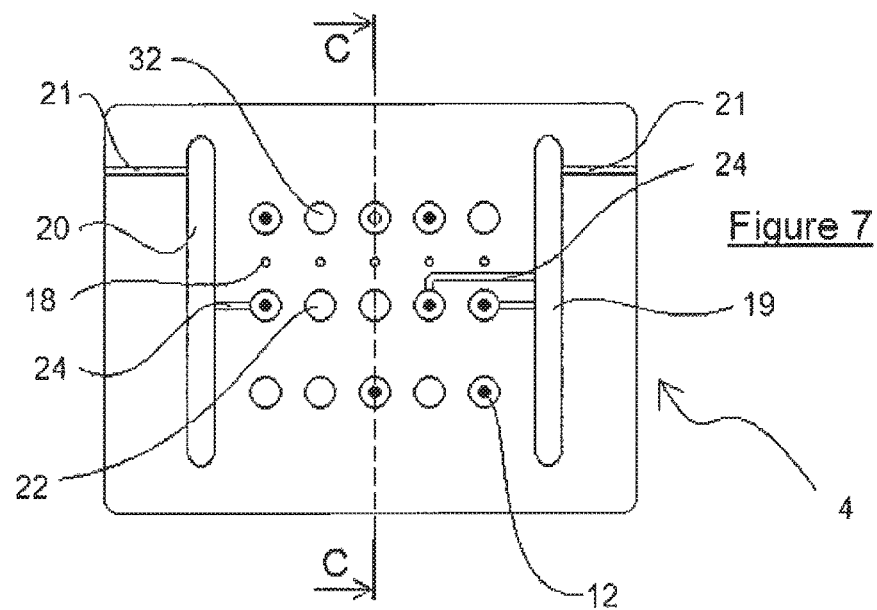
FIG. 7 is a bottom view of the drawer constituting a part of a device according to the invention.

FIG. 7 depicts a more precise view of the drawer 4. It presents vertically five rows of three control means 12, 22 and 32. Each of these groups of three control means corresponds to a step of the method which it is desired to perform. It can be noticed already on this FIG. 7 that the control means 12, 22 and 32 can have three different configurations according to the symbolic system used, namely a white circle, a white circle with a small white circle inside or finally a white circle with a small inner black circle. These uses will be better explained with regard to FIG. 8 a little later.

Note should also be taken of the presence of the indexing holes 18 at each vertical row of control means. Once again, these indexing holes 18 can also be used for the magnetisation by each holding a small magnet.

All of the channels which link the control means 12, 22 and 32 with the upstream 19 or downstream 20 reservoirs bear the reference 24, they are channels for the evacuation of surplus liquids to these reservoirs 19 and 20. Of course for this to be effective, the reservoirs 19 and 20 also communicate to the exterior with the aid of a vent 21, whether this be for the reservoir 19 or for the reservoir 20 to the exterior.

The section C-C of FIG. 8 shows the nature of the control means 12, 22 and 32 at the third line of the control means of FIG. 7, which corresponds to a third step.

It is noted that the control means 12 is pierced with a through hole (a white circle with a small inner black circle) which allows fluidic continuity as will be better described in FIGS. 9 to 14.

For its part, in the case in question, the control means 22 is completely sealed and does not allow any passage of liquid 2 (a white circle).

The third control means 32, for its part, includes a blind hole (a white circle with a small inner white circle) which makes it possible to increase the volume but without allowing the liquid 2 to be evacuated.

FIG. 9 presents a way in which the drawer 4 and the reaction chip 15 can cooperate together to be able to manage the fluidic logics of device 1. The first position is being addressed here. Consequently, the control means will take the references 12P1, 22P1 and 32P1. This position P1 corresponds in FIG. 7 to the vertical alignment of the three control means 12, 22 and 32 situated furthest to the right in this figure.

In this embodiment, the control means 12P1 is a through hole which corresponds to the upstream channel 10 of the chamber 5, which makes it possible for the biological sample 2 to penetrate, in the direction F2, into said reaction chip 15. The liquid 2 will be able to continue its path within said chip 15 by means of the internal pipe 8 and then the external pipe 9; external pipe 9 which for its part cooperates with the control means 22P1 which makes it possible for the liquid to exit in the direction F3.

It should be noted that the volume of the sample 2 is not significant: the liquid containing magnetic beads passes control means 12 to 22. All of the beads are captured in the chip 15 during the passage of the liquid 2 by forming a mass 27. This makes it possible to make a concentration.

It should also be noted that within the chamber 5 the liquid 2 will pass in front of a magnet 26 situated in a lower position of the reaction chip 15. This magnet 26 makes it possible to capture magnetic particles. In this configuration the chamber 6 as well as the downstream channel 11 are not filled with liquid 2 because the control means 32P1 consists of a tight element which does not permit any passage of liquid 2.

It should be noted that the contact surface 13 of the support 3 and therefore, in the present case, of the reaction chip 15 is as smooth as possible in order not to damage the control means 12, 22 and 32 when the sliding in the direction F1 is performed.

FIG. 10 corresponds to the same configuration as FIG. 9, that is to say the control means 12P1 and 22P1 are the extensions of channels 10 and 9, the control means 32P1 being an element which isolates the downstream channel 11. In this embodiment the push in the direction F4 which is similar to F2 is performed by a fluid which tends to push the liquid outwards in the direction F5. This fluid is a gas, preferably air, or a liquid, preferably oil, which does not mix with the liquid 2, whatever it may be (biological sample, elution buffer or other)

Given that the liquid 2 consists of magnetic particles including nucleic acids which have been fixed according to the technique described in patent EP-B-0.389.063, an agglomerate 27 of magnetic particles and nucleic acids is present at the magnet 26. The chamber 6 remains empty.

According to FIG. 11, the drawer 4 is translated in the direction F1 relative to the support 3. Of course, this movement can be the result of either the movement of the drawer 4 relative to the fixed support 3, or of displacement of the movable support 3 relative to the fixed drawer 4, or again, by a relative movement of the drawer 4 relative to the support 3, the two being movable.

In this configuration the control means are modified and become control means 12P2, 22P2 and 32P2. The control means 22P2 is substantially identical to the 22P1 described previously, that is to say it is a through hole which corresponds to the pipe 9. Conversely, in this case, the control means 12P2 is a control means which is liquid-tight, whereas the control means 32P2 is an element which is identical to the control means 22P2, namely it allows the passage of a fluid in the direction F6 to the inside of the downstream channel 11 and to the reaction chamber 6. The liquid 2 can then continue its migration to the internal pipe 8 and then the external pipe 9 to exit again in the direction F7 at the control means 22P2. In this case, the agglomerate 27 of magnetic particles and nucleic acids is still present in front of a magnet 26 which is situated under the chamber 5. This liquid 2 is preferably an elution solution which makes it possible to extract the nucleic acids present on magnetic particles coated in silica, which is the case here and as is particularly described in the patent EP-B-0.389.063.

FIG. 12 presents a third position and therefore a third configuration of the control means 12P3, 22P3 and 32P3. In this case, the central control means 22P3 is closed whereas the third means 32P3 is provided with a through hole. On the other side the first control means 12P3 is equipped with a blind hole which is connected to the upstream channel 10, which makes it possible to increase the volume of air in the chamber 5. As a consequence when a fluid acts in the direction F8 or F9 on the elution liquid 2, this will be able to be displaced in the direction F10 or F11 within the chambers 5 and 6, in order to allow said liquid 2 to perform a movement back and forth within the reaction chip 15. With regard to the back and forth movement, when the air in the control means 32P3 returns to atmospheric pressure, the liquid automatically returns into position in the chamber 6 which allows the nucleic acids and the reaction chip 29 to be placed in contact. This will be facilitated by the presence of air within the first control means 12P3 which will be compressed and expanded depending on the force applied by the fluid in the direction F8 or F9. This configuration allows the passage and return of the elution liquid 2 a certain number of times at the agglomerate of magnetic particles and nucleic acids 27, the aim being to allow the nucleic acids to be detached and to be absorbed within the elution liquid 2.

In FIG. 13, the three control means 12P4, 22P4 and 32P4, according to this fourth configuration, are all sealed. In this position, the liquid 2 is returned into its initial position, that is to say that the air trapped in the chamber 5 is returned into its initial position since there is no longer pressure in the direction F8 or F9. It is in this position that the incubator 17, described in FIG. 2, will make it possible to heat the chamber 6, and optionally the chamber 5, in order to incubate said liquid 2.

In chamber 5, a first incubation at 40° C. is performed for 5 minutes. The second incubation proceeds at 65° C. for 16 hours in chamber 6, preceded by a denaturation at 90° C. for a few minutes.

Another difference is of course that the agglomerate present in the chamber 5 in front of the magnet 26 is an agglomerate 28, which now only consists of magnetic particles, the nucleic acids having been to a very great extent, or even totally, absorbed by the elution liquid 2.

Finally, FIG. 14 shows that, in this fifth configuration, the control means 12P5 is closed, the control means 22P5 is open and allows a fluid to enter in the direction F12. And finally the third control means 32P5 is also open to allow the evacuation of the elution liquid 2 in the direction F13. In this case in question, it is very evident that the nucleic acids have been captured by capture nucleic acids, called detection probes, fixed on the reaction chip 29. There will therefore be hybridisation between the capture reaction chip 29 and the nucleic acids, which were present in the starting biological liquid 2. As a result it will be possible, with the aid of the window 31, to carry out a reading within the reaction chip 15 to know whether or not hybridisation has taken place. Of course, this reaction chip 29 can include one or more spots which allow the analysis of the presence of one or more types of nucleic acids of interest.

Operation Principles and Conditions
Information in Addition to that which has been Described Above:

The principle of the device 1, according to the invention, is to make the control means, called seals, 12, 22 and 32, slide on the hybridisation reaction chip 15 during the protocol. There are three seals for each step of the protocol: one per hole in the chip 15. Either the seal is plugged and the valve is closed, or the seal is pierced and the valve is open. The injection via the open seals is done by elastic sealing between the injection means (pipette cone joined to a pipette for example) and the elastic seal. The seals are distributed on a plastic drawer 4 so as to reproduce the steps of the protocol. The part of the seals which bears on the chip is thicker than the plastic card to ensure a good tightness.

The liquids 2 are injected with the aid of a cone present at a pipette (manual operation) or an instrument (automatic operation).

The movable drawer 4 slides in the support 3 between several successive positions (position tolerance is: +/−0.4 mm). The seals are solely in contact with the chip 15, but not with the rest of said support 3. The volume of this chip 15 is in the region of 1 μL.

In another embodiment of the device 1, this bears a hybridisation reaction chip 29, included in a plastic chip or a glass chip of the Micronit® 15 brand, and an incubator 17.

The magnets 26 have a diameter of 1.5 mm, a length of 3 mm and are integrated in a fixed part under the chip 15. They consist of neodymium-iron-boron of a residual magnetism of approximately 1.2 Tesla.

The complete dimensions of said device 1 are 10 cm in length by 4.5 cm in width and 2 cm in height and respectively 5.5 cm by 3.5 cm and 0.5 mm in height for the drawer 4. These values have been selected to facilitate manufacture and use, but could be easily modified, whether it be upwards or downwards.

The volume of the hybridisation and elution liquid must allow a complete filling of the chamber 6. The volume of each chamber is between 0.1 and 100 μl, preferably between 0.1 and 10 μl and still more preferably between 0.1 and 1 μl. In fact, a chamber has a volume of 0.25 μL, 0.5 to 0.8 μL of hybridisation buffer is introduced. Of course, the exact volume is defined during the translation in the direction F1.

Furthermore, the air is injected with a pipette tip and the necessary pressure can be controlled manually or automatically to allow the transfer of liquid 2. The pressure is constant during the entire elution, which is 5 minutes at 40° C.

Plastic Chip:

The chip 15 is machined from PMMA or PTFE. The channels are 500 μm wide and 200 μm high. The hybridisation volume is in the region of 1 μL. The length, the width and the thickness of said chip 29 is 18 mm, 4 mm and 450 μm. More precisely with regard to the thickness, the body (upper part) and the cover (lower part) have a thickness of between 30 to 400 μm, preferably a thickness of 170 to 400 μm at the reading areas.

The channels are closed by an ARseal™ adhesive film (Ref.: DEV-90404 of the company Adhesive Research—Glen Rock, Pa., USA) with a thickness of 150 μm.

It should be noted that, to facilitate the sticking of the adhesive onto the chip 15, it is necessary to heat the chip and the adhesive to a temperature of around 75° C.

Micronit Glass Chip:

This chip which is of identical dimensions to the preceding one has two chambers 5 and 6. The chamber 5 makes it possible to capture the magnetic beads and has dimensions which are comparable to and compatible with those of the magnets 26 (D: 1.5 mm, L: 3 mm). This chip 29 was manufactured by the company Micronit (Enschede, The Netherlands).

Materials Used or Able to be Used:

The chip 29 has been described above made of PMMA plastic or glass, but it could also easily be made of silicon, metal or any type of hard plastic which is impermeable to gases and liquids, such as Teflon, for example. It is preferable to chamfer the chip 15, particularly made of glass, for example on an abrasive surface of the glass-paper type, to promote the sliding in the direction F1 without tearing the seals on the edge of the chip.

The device 1 is machined from PolyMethyl MethAcrylate, called PMMA.

The seals are moulded in silicone B.A.D. from Plastiform (Ref.: 310 120 15N, Thise, France) or from butyl rubber or polyisobutylene, referred to as Butyl Rubber. These extend beyond the contact surface by a height of between 100-300 μm.

EXAMPLES

Example 1: Pressurisation of a Liquid Segment (Plastic or Glass Chip)

A—Objective:

The objective is to control the position of the liquid segment during a 10 minute pressurisation. The indicator is the good return of the liquid into the initial position.

B—Tests:

The device 1 is configured as in FIG. 11, that is to say with control means 12P2 closed and control means 22P2 and 32P2 open. The hybridisation chamber 6 is filled to excess with a liquid 2. Said device 1 is then translated in the direction F1 into the configuration of FIG. 12, that is to say with control means 32P3 open and control means 12P3 closed by a blind hole and 22P3 closed. The chip 15 is pressurised by means of a pump linked to a cone inserted into the open seal. The pressure is regulated at 1 bar (relative to Patm) and checked at the manometer (Keller 70621) at regular intervals.

The liquid migrates from the hybridisation chamber to the environment of the capture chamber.

C—Results:

This experiment was performed three times. No movement of the liquid segment is recorded over 10 minutes. When the pressure is relaxed, the liquid segment returns to the initial position (visual inspection). Ten pressurisations to 1 bar and relaxation of a few seconds does not influence the final position of the liquid segment. This has been carried out without movement of the device in the direction F1 between the pressurisations.

The pressure limit is determined by regularly increasing the pressure until a leak appears. The device 1 has a pressure limit greater than 4 bars, that is to say without a leak during the pressurisation on the compressed air network. The results are identical whether the chip is made of plastic or glass.

Example 2: Management of the Fluids (Plastic or Glass Chip)

A—Objective:

The objective is to test the basic functions of device 1, namely and particularly the tightness of the seals, the flow, the ease of use, etc.

B—Tests:

Different configurations were tested:
filling of a channel,
sliding in the direction F1 of the device 1 after filling of a channel,
filling of the other channel when the first is filled, and
emptying a channel and associated chamber.

C—Results:

The filling of a channel (two control means or two valves open and one closed) is very easy. The cone is inserted easily and creates a perfectly tight link. The liquid exits via the other open valve. The liquid segment does not move (visual inspection) when the movable drawer 4 changes position. It is thus possible to fill the second channel without modifying the position of the first liquid segment. The emptying of the channels is carried out by circulating air.

Example 2: Incubation of 16 Hours at 65° C. (Plastic or Glass Chip)

A—Objective:

The incubation inside a plastic chip is the critical step of the protocol. Thus, various difficulties can arise.

Firstly, problems associated with the chip, regarding the adhesive, the plastic and the diameters of the holes. Furthermore, in the long term (duration above 5-7 hours), there can be an absorption or an evaporation via the adhesive or the chip itself. Finally, bubbles can form from the adhesive.

Problems associated with the seals can also appear. In the short and long terms, there can be leaks or evaporations at the three seals.

B—Tests: Materials and Methods

For this study, we used:
a camera (for example Sony Handycam) to record incubations of 16 hours and more.
a regulated EasyQ incubator to obtain a temperature of 65° C. at the chip for the plastic chips.
the incubator integrated into the device according to the invention for the Micronit® chips.
dyed water for the first experiments and then Agilent hybridisation buffer (Ref. 2x Hi-RPM Hybridization Buffer 5190-0403, Santa Clara, Calif., USA) dyed for validation.

C—Tests: Work Performed on the Plastic Chip

List of the adhesives which give acceptable results:
ARseal™ DEV-90404-100 µm COP Carrier, Coated with Silicone PSA 50 µm, and
ARseal™ DEV-90697-50 µm PP, Coated with Silicone PSA.

These two adhesives are suitable for the sealing of the plastic chips (heat-sealing).

The chip can be made of teflon (PTFE) in order to limit the absorption and the evaporation through the chip.

The holes through the chip are 200-300 µm in order to limit the liquid-seal contact.

These conditions are sufficient to produce a sealed plastic chip under the standard hybridisation conditions.

D—Tests: Work Performed on the Seals

D1—Suitability of the Materials for the Seals:

The tables below describe the properties of permeability and water absorption of different polymers.

The incubation tests were firstly carried out on silicone blocks on grounds of ease of production despite their poor physical properties. We use seals made of butyl rubber, a material which is one of the most tight.

TABLE 1

Absorption of water by different materials

| Material | Water absorption coefficient (% in 24 hours) | Permeability of the vapour at 25° C. ($\times 10^{-13}$ cm$^3$ · cm cm$^{-2}$ s$^{-1}$ Pa$^{-1}$) |
|---|---|---|
| PMMA | 0.2-0.3 | 500 |
| Polyamide | 0.3 | |
| Polyacetal | 0.3 | |
| Polypropylene (PP) | 0.03 | 16 (70 to 38° C.) |
| PTFE (Teflon) | 0 | 25 |
| Polystyrene (PS) | 0.8 | |
| PEEK | 0.1-0.3 | |
| PolyEthylene | <0.01 | |
| High Density PolyEthylene (HDPE) | <0.01 | 10 (40 to 38° C.) |
| PVC | 0.03-0.4 | |
| Polyester | 0.02-0.03 | |
| PET | <0.7 | 200 to 38° C. |
| Butyl rubber | <0.2 | << to 10 |

TABLE 2

Permeability to gases for polymers in the medical sector

| | $O_2$ | $N_2$ | $CO_2$ | $H_2$ | $H_2O$ (1) |
|---|---|---|---|---|---|
| Parylene C | 2.8 | 0.4 | 3 | 43 | 0.08 |
| Parylene D | 12 | 1.8 | 5 | 94 | 0.1 |
| Parylene N | 15 | 3 | 84 | 213 | 0.6 |
| HDPE | 73 | 17 | 228 | n.d. | 0.12 |
| PS | 138 | 23 | 400 | n.d. | 3.5 |
| PTFE | 223 | 133 | n.d. | 516 | n.d. |

TABLE 2-continued

Permeability to gases for polymers in the medical sector

|  | $O_2$ | $N_2$ | $CO_2$ | $H_2$ | $H_2O$ (1) |
|---|---|---|---|---|---|
| LDPE | 140 | 80 | 700 | n.d. | 0.6 |
| PC | 124 | 22 | 827 | n.d. | 1.5 |
| FEP | 295 | 126 | 657 | 381 | 0.16 |
| Silicone | 19000 | n.d. | 118000 | 17000 | 3 |

(1) $H_2O$ in $cm^3 \cdot mm/m^2 \cdot day \cdot atm$
All of the gases are expressed in $g \cdot mm/m^2 \cdot day$

TABLE 3

Permeability to gases of materials

| Materials | fluid | Permeability at 20° C. *$10^7$ g/(m · s · bar) |
|---|---|---|
| Chloroprene | $H_2O$ | 0.1 to 1.3 |
| Polyurethane (PU) | $H_2O$ | 1 to 5 |
| PU | $H_2O$ | 0.7 to 2.6 |
| Nitrile rubber | $H_2O$ | 1 to 2 |
| Hypalon rubber | $H_2O$ | 0.5 |
| Natural rubber | $H_2O$ | 2.5 |
| Natural rubber | $H_2O$ | 1.7 |
| Butyl rubber | $H_2O$ | 0.73 |
| Butyl rubber | $H_2O$ | 0.9 |
| Chloroprene | $O_2$ | 0.022 |
| Natural rubber | $O_2$ | 0.13 |

E—Tests: Incubation in Plastic Chip

E1—Various Materials:

Various materials were tested for the seals. The experimental protocol is an incubation for several hours at 65° C. in a device of which the seals of the incubation step have been modified. An item, not shown in the Figures, which compresses the seals can be screwed onto the fixed part of the device, which improves the system's tightness.

The first step is an incubation of dyed water in the whole component. In the event of success, the second step is an incubation of slightly dyed hybridisation buffer in half of the chip (same protocol).

The loss of liquid is close to 1 µL of the initial 2 µL.

Upon dismounting, it is observed that the seal has taken the form of the chip (holes and surface roughness).

The loss is estimated at 46% in 16 hours of incubation.

This amounts to a leak of 1 µL in 16 hours which corresponds to a leak of 0.33 µL per seal and per incubation.

E2—Blocks Made of D.A.V (Silicone) Variant of B.A.D:

After 4 hours, it is clearly seen that the liquid is disappearing at the seals. Now, the seals are pressed firmly onto the surface. After 6 hours, there is a little progression. Finally, after 21 hours and taking account of the time passed, there has been little progression of the evaporation.

The loss is estimated at 35% in 21 hours, which equates to 27% in 16 hours.

E3—Tests in Sealed Capillaries: Estimation of the Liquid Loss in a Silicone Seal:

Two glass capillaries (inner diameter 500 µm, that is to say equivalent to the diameter of the hole in the plastic chip) are filled with dye and sealed at the ends with a B.A.D silicone seal and an epoxy glue, which acts as a reference.

After a week of incubation at a temperature of between 65 and 70° C., the volume evaporated from the capillary is around 2 µL. This result represents an average evaporation of 0.1 µL per hole and per incubation of 16 hours. The loss due to the seal therefore should not exceed 0.3 µL during the incubations on plastic chips, because there are three holes in the reaction chip.

With tests over 70 hours on 5 mm of capillary, a volume of 1 µL is evaporated. This confirms the figure of 0.34 µL of loss per incubation per silicone seal. This material is therefore of little interest.

E4—Seals Made of Natural Rubber (Natural Rubber NR):

The loss is estimated at 19% in 16 hours.

The lower seal is faulty, perhaps following ripping apart during displacement of the movable part. The leak ascertained can be a consequence of this. This material is sensitive to shearing (tearing).

E5—Blocks Made of Butyl Rubber (Butyl Rubber):

$1^{st}$ Experiment:

This material is tighter than the silicone tested previously. The liquid loss is estimated at 24% over 22 hours. This equates to 17% over 16 hours of incubation.

$2^{nd}$ Experiment:

For this experiment, the diameter of the holes in the chip has been modified.

The holes in the chip are 200 µm in diameter instead of 500 µm previously.

No leak or evaporation is ascertained. The first step is validated.

$3^{rd}$ Experiment:

A temperature probe was added under the chip (piercing of the fixed part of the device) in order to monitor the temperature during the entire incubation.

No evaporation appears during the first 15 hours. At 16 hours, a start of a leak is observed which grows steadily but which remains below 5% of the volume.

$4^{th}$ Experiment:

Only half of a liquid segment (1 µl) is used with the hybridisation buffer.

This is dyed in order to make it possible to see the progression of the liquid segment.

No leak is ascertained. Butyl rubber is a material which is suitable for the incubation step.

The seals of the device are therefore made of two different materials, namely: silicone for the fluidic steps and butyl rubber for the incubation step.

$5^{th}$ Experiment:

The preceding handling was repeated. The conclusion is identical. The incubation was extended to 87 hours in order to estimate the limits of the system.

F—Tests: Incubation in Glass Chip

The incubation step in the Micronit® chip is critical because the hybridisation volume is 250 nL (volume of a half-chamber).

The incubator is integrated into the base of the device. The temperature increase time is in the region of 15 minutes. The passage from incubation in a plastic chip to a glass chip poses no major problem. The reduction of the incubation volume from 1 µL to 0.25 µL has no impact upon the results.

The choice of material for the seal for the incubation is butyl rubber, linked with a hole diameter of the microfluidic chip of 200 µm, it guarantees an excellent tightness at 65° C. over durations greater than 17 hours.

This material is not obligatory. In the case of mass production, other injectable materials, known to the person skilled in the art, could be envisageable.

Example 3: Pre-Incubation at 90° C.

A—Objective:

In one of the steps of the operations, provision is made for a temperature increase to 90-95° C. before the incubation proper at 65° C. This step was performed followed by an incubation of 24 hours at 65° C. (FIG. 15).

B—Tests:

Half of the chip is filled with hybridisation buffer, respecting the protocol (step represented in FIGS. 11 and 12). The chip is closed (step represented in FIG. 13) for incubation.

The incubator is pre-adjusted to heat the chip to 90° C. Once the temperature is reached, the incubator is adjusted to 65° C. The chip therefore falls again gradually in temperature to 65° C. for the incubation.

C—Results:

Neither liquid movement nor evaporation were detected after 24 hours of incubation.

Example 4: Integration of the Incubator into the Device

The incubator has been calibrated so that the temperature is around 65° C. in the microfluidic chip. To do this, two heat probes are placed into a false microfluidic plastic chip. FIGS. 16 and 17 show:

FIG. 16: the temperature stabilisation with a standard deviation of 0.1° C. (average 63.5° C.) over 3 hours, and FIG. 17: the heating of the test device in 20 minutes.

Example 5: Magnetic Particle Flow Capture

A—Objective:

The objective is to characterise the effectiveness of the flow capture of magnetic beads in the microfluidic component.

B—Tests:

With regard to the solution present in the device, theory and practice show that magnets having dimensions in the region of millimeters are sufficiently large to capture small magnetic particles of a size or diameter of 0.1 to several µm, present in a microfluidic chamber, while the distance between magnet and chamber is less than 400 µm. In the case of our device, the reaction chip 15 has a glass cover with a thickness of 170 µm and the magnet is 3 mm long and 1.5 mm in diameter. Nevertheless, the speed of the flow must be less than 10 µL/min to allow an effective capture of at least 90% of the magnetic particles.

The magnetic capture particles have shown an effective capture with the device according to the invention. With a flow speed of 5 µL/min, and for three different experiments, the effectiveness of the capture has been 95, and 97%, for amino Adembeads magnetic particles of 200 nm in diameter [Ref. AMINO-ADEMBEADS 200 nm, Ademtech, Pessac, France] (1.6 µL in 50 µL of capture buffer). For comparison, an efficiency of greater than 95% was obtained with a manual protocol.

Example 6: Agitation

A—Objective:

To further improve the performances, it is possible that agitation will be necessary during incubation. It must aid the diffusion and the distribution of RNA in the sample.

B—Tests: Agitation by Ultrasound in an Ultrasound Bath

The end objective is to be able to carry out the agitation during the hybridisation by ultrasound. Firstly, we tested the mixture of two dyes in an ultrasound bath.

The first segment of a 1 µL plastic chip is filled with dyed water (1 µL) and the second with undyed water (1 µL). The assembly is sealed into a silicone seal identical to the seals of the device.

A first assembly is placed into the ultrasound bath. The mixture is carried out visually in 1 to 2 minutes.

A second assembly is left at ambient temperature outside of the bath. The mixture is therefore solely the consequence of a simple diffusion. After 17 hours, the colour of the chip is not homogenous even if the dye is present throughout the chip.

C—Test: Agitation by Ultrasound in Capillary

A glass capillary, with a diameter of 520 µm, is coupled to an ultrasound transducer operated by a frequency generator. The dispersion of magnetic beads attracted beforehand by a magnet is observed. The frequency is 50-150 kHz.

This technique appears effective although this experiment does not allow a conclusion to be reached (test in capillary and not in chip, piezoelectric transducer in contact with the capillary and not carried in the incubator). It has the advantage of being easy to implement compared to other solutions such as a SAW (Surface Acoustic Wave) Advalytix probe (Ref. SlideBooster SB450, Munich, Germany). The integration of this solution can be accomplished by simply integrating a piezoelectric element in the incubation unit.

The redispersion of a plug of magnetic beads in a glass capillary by means of the ultrasounds is therefore possible. The redispersion time is less than 5 seconds.

D—Test: Thermal Agitation

One half of the device is filled with dyed water and the second is filled with water. A slow spread of the coloration is observed. This technique is not effective.

Example 7: Integration of the Device in an Instrument

A—Validation of the Device: Purely Manual Use

The management of the fluids of the device is accomplished by tightness between a cone, or pipette tip, and a flexible seal. The majority of cone types are compatible with the current device. The entirety of the hybridisation steps can therefore be carried out by hand by a trained technician.

The most critical step is the capture of the magnetic particles. If the capture is flow capture, a simple device, of the type of the syringe of the Agilent BioAnalyzer (Bioanalyzer 2100, Santa Clara, Calif., USA): based on a defined fluidic resistance coupled to a volume of pressurised air) which makes it possible to circulate the starting sample at around 5 µL/min in the device, regardless of the volume of the sample. The hybridisation can be carried out in an oven.

The advantages of this device are that it is:

very simple, very inexpensive, with a restricted risk of pipetting error, perfectly suited to a need for a few tests per day.

The disadvantages are that it:

requires a full-time operator for the preparation phases, and has an incubator, an agitator and a reader outside the system or which have to be additionally integrated.

B—Validation of the Device: Semi-Automatic System

In this version only the pipetting steps are accommodated by the system. The incubator, the agitator and the reader are outside the system.

The instrument is based on an arm for pipetting on two axes Y/Z which takes and deposits cones, aspirates the reagents and ejects them into the device. After each step, a one-axis arm or table offsets the device and the reagents by one notch. The pipetting apparatus thus has access to new cones and new reagents.

Within the framework of automisation of the device according to the invention, there are particular advantages, which are that it:
- is inexpensive (no incubator and no reader),
- is small in size, and
- simplifies the work of a technician.

Conversely, the disadvantages are that there is:
- little added value compared with the manual solution,
- requirement of the presence of an operator for the incubation and reading steps,
- a significant development time and cost, and
- additional design of dedicated consumables.

C—Validation of the Device: High-Speed System

This instrument configuration manages the pipetting, the displacement of the devices from storage area to the fluidic area and then to the incubators and the reader. Everything is managed by a single robot arm acting as pipetting means. This type of displacement in an instrument already exists for microplate formats. The instrument is therefore based on existing three-axis platforms, such as Hamilton (Ref.: Starlet, Hamilton Robotic, Bonaduz GR, Switzerland), Tecan (Männedorf, Switzerland).

The agitator and the optical reader are also specially developed.

The technician inserts racks of samples, reagents, cones and devices according to the invention into the machine. If the fluids handling time is one hour per test, it can work on its own for approximately 15 tests such that the machine can function all night without needing to be reloaded.

In this case, the advantages are that:
- the solution is integrated,
- the user fills the machine two times per day, and
- the device is based on an existing platform.

REFERENCES

1—Device for preparation, treatment and/or analysis
2—Biological sample or any other liquid
3—Reaction support of the device 1
4—Drawer of the device 1
5—Transfer chamber of the support 3
6—Reaction chamber of the support 3
7—Central channel
8—Internal pipe linking the two chambers 5 and 6
9—External pipe linking the internal pipe 8 which emerges to the exterior
10—Upstream channel of chamber 5 which emerges to the exterior
11—Downstream channel of chamber 6 which emerges to the exterior
12—Control means which cooperate with the emerging channel
13—Contact surface of the support 3 where the channels 9, 10 and 11 emerge
14—Base of the support 3
15—Reaction element or reaction chip of the support 3
16—Reading area of the chamber 6
17—Incubator
18—Indexing hole or position of the magnet
19—Upstream reservoir for collecting surplus liquids
20—Downstream reservoir for collecting surplus liquids
21—Vent between reservoirs 19 and 20 and the exterior
22—Control means which cooperate with the emerging channel 9
23—Slideways which make possible the translation of the drawer 4 relative to the support 3
24—Channels for evacuating the surplus liquids to the reservoirs 19 and 20
25—Groove in the contact surface 13 which allows the passage of the means 12, 22 and 32
26—Magnet
27—Agglomerate of magnetic particles and nucleic acids
28—Agglomerate of magnetic particles
29—Reaction chip of the element 15
30—Reading window of the base 14
31—Reading window of the element 15
32—Control means which cooperate with the emerging channel 11
F1—Translatory movement of the drawer 4 relative to the support 3
F2—Introduction of a biological sample 2 at the control means 12P1
F3—Exit of sample 2 under the action of F2 at control means 22P1
F4—Introduction of air at control means 12P1
F5—Exit of sample 2 under the action of F4 at control means 22P1
F6—Introduction of elution liquid 2 at the control means 32P2
F7—Exit of the liquid 2 under the action of F6 at control means 22P2
F8—Introduction of air at control means 32P3
F9—Exit of air at control means 32P3
F10—One-way movement of the liquid 2 due to the movement F8 creating a back-and-forth movement with F9
F11—Return movement of the liquid 2 due to the movement F9 creating the back-and-forth movement with F8
F12—Introduction of air at control means 22P5
F13—Exit of the liquid 2 under the action of F12 at control means 32P5
P1—Starting position of the drawer 4 relative to the support 3
P2—Position of the drawer 4 relative to the support 3 after a first translation
P3—Position of the drawer 4 relative to the support 3 after a second translation
P4—Position of the drawer 4 relative to the support 3 after a third translation
P5—Finishing position of the drawer 4 relative to the support 3 after a last translation

The invention claimed is:

1. A device for preparation, treatment and/or analysis of at least one liquid, optionally a biological sample, comprising:
a reaction support (3), comprising
a reaction element comprising
a set of at least two chambers comprising a first chamber (5) and a second chamber (6), the set further comprising:
at least one central channel (7) comprising:
an internal pipe (8) operable to allow the chambers (5 and 6) to be linked to one another in fluidic communication so as to constitute a set of adjacent chambers, and
an external pipe (9) operable to link the internal pipe (8), by fluidic communication, to the exterior, and
at least one emerging upstream channel (10) situated upstream of the first chamber (5) and at least one emerging downstream channel (11) situated downstream of the second chamber (6), each operable to link the respective chamber, by fluidic communication, to the exterior, and a drawer (4), which is movable in translation relative to the reaction support (3), between at least two translatory positions (P1 and P2), and having, for each position, at least a first control element (12), a second control element (22) and a third control element (32) operable to cooperate to close and/or to open the emerging upstream channel (10), external pipe (9) and downstream channel (11), respectively, in order to bring the internal volume of the chambers into (open control element) or out of (closed control element) fluidic communication with the exterior of the device, wherein the channels cooperate with the control elements borne by the drawer (4): a first control element (12) operable and aligned to cooperate with the emerging upstream channel (10), a second control element (22) operable and aligned to cooperate with the external pipe (9), and a third control element (32) operable and aligned to cooperate with the emerging downstream channel (11), and wherein each control element (12, 22 and 32) of the drawer (4) comprises a seal configured to cooperate with a contact surface (13) of the reaction support (3) at each translatory position.

2. The device according to claim 1, wherein the reaction support (3) further comprises:
a base (14) comprising a slideway and/or grooves on a contact surface of the base which allow the drawer to move slideably in translation, and
a reaction element (15) comprising the first and second chambers (5 and 6), the internal pipe (8), the external pipe (9) and the upstream and downstream channels (10 and 11).

3. The device, according to claim 2, wherein the reaction element (15) further comprises:
a reaction chip (29), and
a reading window (31) which makes detection possible at the chip (29).

4. The device according to claim 1, wherein each control element (12, 22 and 32) of the drawer (4) comprises a seal capable of cooperating with the contact surface (13) of the reaction support (3) at each translatory position (P1, P2, P3, P4 and/or P5).

5. The device according to claim 1, wherein all of the chambers (5 and 6), channels (9, 10 and 11) and control means (12, 22 and 32) in fluidic relationship are aligned relative to one another for each translation position (P1, P2, P3, P4 and/or P5).

6. The device according to claim 1, being configured for separation and incubation of a liquid biological sample, wherein the first chamber and the second chamber being adjacent, the first chamber being a transfer chamber, and the second chamber being a reaction chamber.

7. The device according to claim 1, wherein the second chamber (6) includes a reading area (16).

8. The device according to claim 1, wherein the drawer (4) includes in at least one position a magnet capable of acting on at least one of the chambers (5 or 6) to allow the separation of magnetic particles if present in the liquid.

9. The device according to claim 1, wherein the reaction support (3) includes in at least one position a magnet capable of acting on at least one of the chambers (5 or 6) to allow the separation of magnetic particles if present in the liquid.

10. An analysis apparatus for the implementation of a device according to claim 1, the apparatus comprising:
a device according to claim 1,
a driver allowing the relative movement of the drawer (4) relative to the reaction support (3), and
a pipetting apparatus for transferring within the device (1) all or part of a liquid, wherein the liquid can be a biological sample to be treated or a reagent liquid(s) (washing liquid, elution liquid).

11. The apparatus according to claim 10, intended to allow the incubation of the biological sample, further comprising an incubator positioned for heating the biological sample in the first and/or second chamber.

12. The apparatus according to claim 10, comprising, at the pipetting apparatus, a pipette tip or a needle capable of cooperating with each of the control means (12, 22 and 32) at each translator position.

13. A method of using a device according to claim 1, wherein:
a liquid is introduced into the first chamber (5) by injecting it into the first control element (12), by opening the second control element (22) and by closing the third control element (32), or
a liquid is introduced into the first chamber (5) by injecting it into the second control element (22), by opening the first control element (12) and by closing the third control element (32), or
a liquid is introduced into the second chamber (6) by injecting it into the second control element (22), by opening the third control element (32) and by closing the first control element (12), or
a liquid is introduced into the second chamber (6) by injecting it into the third control element (32), by opening the control element (22) and by closing the first control element (12), or
a liquid is introduced into the first and second chambers (5 and 6) by injecting it into the first control element (12), by opening the third control element (32) and by closing the second control element (22), or
a liquid is introduced into the first and second chambers (5 and 6) by injecting it into the third control element (32), by opening the first control element (12) and by closing the second control element (22), or
a liquid present in the first chamber (5) is purged by injecting or by aspirating a fluid into the first control element (12), by opening the second control element (22) and by closing the third control element (32), or
a liquid present in the first chamber (5) is purged by injecting or by aspirating a fluid into the second control element (22), by opening the first control element (12) and by closing the third control element (32), or
a liquid present in the first chamber (5) is purged by injecting or by aspirating a fluid into the third control element (32), by opening the first control element (12) and by closing the second control element (22), or
a liquid present in the first chamber (5) is purged by injecting a fluid into the first control element (12), by opening the third control element (32) and by closing the second control element (22), or
a liquid present in the second chamber (6) is purged by injecting or by aspirating a fluid into the second control element (22), by opening the third control element (32) and by closing the first control element (12), or
a liquid present in the second chamber (6) is purged by injecting or by aspirating a fluid into the third control element (32), by opening the second control element (22) and by closing the first control element (12), or
a liquid present in the second chamber (6) is purged by injecting or by aspirating a fluid into the third control element (32), by opening the first control element (12) and by closing the second control element (22), or a liquid present in the second chamber (6) is purged by injecting or by aspirating a fluid into the first control element (12), by opening the third control element (32) and by closing the second control element (22), or a liquid present in the first and second chambers (5 and 6) is purged by injecting or by aspirating a fluid into the first control element (12), by opening the third control element (32) and by closing the second control element (22), or a liquid present in the first and second chambers (5 and 6) is purged by injecting or by aspirating a fluid into the third control element (32), by opening the first control element (12) and by closing the second control element (22), or a liquid present in the first and second chambers (5 and 6) is purged by injecting or by aspirating a fluid into the second control element (22), by opening the first and third control elements (12 and 32), or a liquid is incubated in the first chamber (5) by closing the first and second control elements (12 and 22) and by applying a source of heat to said first chamber (5), or a liquid is incubated in the second chamber (6) by closing the second and third control elements (22 and 32) and by applying a source of heat to said second chamber (6), or a liquid is incubated in the first and second chambers (5 and 6) by closing the first, second and third control element (12, 22 and 32) and by applying a source of heat to said first and second chambers (5 and 6), or a precise volume of a liquid is sampled at the first chamber (5), firstly, by opening the first and second control elements (12 and 22), by closing the third control element (32) and pushing, with the aid of a fluid, the liquid, via the first control element (12), until it overflows at the second control element (22), and finally by translating the drawer (4) relative to the support (3), or a precise volume of a liquid is sampled at the first chamber (5), firstly, by opening the first and second control elements (12 and 22), by closing the third control element (32) and pushing, with the aid of a fluid, the liquid, via the second control element (22), until it overflows at the first control element (12), and finally by translating the drawer (4) relative to the support (3), or a precise volume of a liquid is sampled at the second chamber (6), firstly, by opening the second and third control elements (22 and 32), by closing the first control element (12) and pushing, with the aid of a fluid, the liquid, via the second control element (22), until it overflows at the third control element (32), and finally by translating the drawer (4) relative to the support (3), or a precise volume of a liquid is sampled at the second chamber (6), firstly, by opening the second and third control elements (22 and 32), by closing the first control element (12) and pushing, with the aid of a fluid, the liquid, via the third control element (32), until it overflows at the second control element (22), and finally by translating the drawer (4) relative to the support (3), or a precise volume of a liquid is sampled at the first and second chambers (5 and 6), firstly, by opening the first and third control elements (12 and 32), by closing the second control element (22) and pushing, with the aid of a fluid, the liquid, via the first control element (12), until it overflows at the third control element (32), and finally by translating the drawer (4) relative to the support (3), or a precise volume of a liquid is sampled at the first and second chambers (5 and 6), firstly, by opening the first and third control elements (12 and 32), by closing the second control element (22) and pushing, with the aid of a fluid, the liquid, via the third control element (32), until it overflows at the first control element (12), and finally by translating the drawer (4) relative to the support (3), or a movement of a liquid back and forth is carried out at the first chamber (5), firstly by injecting it into the first control element (12), by opening the second control element (22) and closing the third control element (32), then, by translating the drawer (4) relative to the support (3) into a position which closes the second control element (22), and finally by at least once pushing, with the aid of a fluid, through the first control element (12), the liquid present in the first chamber (5) towards or into the second chamber (6) by compressing the air trapped in the second chamber (6), or a movement of a liquid back and forth is carried out at the first chamber (5), firstly, by injecting it into the second control element (22), by opening the first control element (12) and closing the third control element (32), then, by translating the drawer (4) relative to the support (3) into a position which closes the second control element (22), and finally by at least once pushing, with the aid of a fluid, through the first control element (12), the liquid present in the first chamber (5) towards or into the second chamber (6) by compressing the air trapped in the second chamber 6, or a movement of a liquid back and forth is carried out at the second chamber (6), firstly by injecting it into the second control element (22), by opening the third control element (32) and closing the first control element (12), then, by translating the drawer (4) relative to the support (3) into a position which closes the second control element (22), and finally by at least once pushing, with the aid of a fluid, through the third control element (32), the liquid present in the second chamber (6) towards or into the first chamber (5) by compressing the air trapped in the first chamber (5), or a movement of a liquid back and forth is carried out at the second chamber (6), firstly by injecting it into the third control element (32), by opening the second control element (22) and closing the first control element (12), then, by translating the drawer (4) relative to the support (3) into a position which closes the second control element (22), and finally by at least once pushing, with the aid of a fluid, through the third control element (32), the liquid present in the second chamber (6) towards or into the first chamber (5) by compressing the air trapped in the first chamber (5).

14. The method, according to claim 13, wherein, when a liquid present in the first and/or second chambers (5 and/or 6) is purged by injecting a fluid through a first, second or third control element (12, 22 or 32) and evacuating it via another control element (12, 22 or 32), this other control element (12, 22 or 32) is linked to a reservoir (19 or 20) for collecting the surplus liquids via a channel (24).

15. The method for separation and incubation of nucleic acids in a liquid within a device according to claim 1, comprising the following steps:

with the drawer at a first translatory position, a liquid, containing nucleic acids of interest captured on magnetic beads, is introduced into the first chamber (5) by injecting it into the first control element (12), while opening the second control element (22) and closing the third control element (32), any surplus liquid exiting into a collection reservoir (20) via a channel (24), a magnet (26) present in the vicinity of the first chamber (5), captures the magnetic particles and the nucleic acids, then the liquid present in the first chamber (5) is purged by injecting air into the first control element (12), whilst keeping the third control element (32) closed, and once again any surplus liquid exits into the collection reservoir (20) via the channel (24), the drawer (4) is translated relative to the support (3) into a second translatory position in which there is still a magnet in the vicinity of the first chamber (5), a precise volume of an elution liquid is sampled at the chamber (6), firstly, the second and third control elements (22 and 32) being open and the first control element (12) being closed and the liquid is pushed, via the third control element (32), until it overflows at the second control element (22), the support (3) is translated relative to the drawer (4) into a third translatory position in which there is still a magnet in the vicinity of the first chamber (5), a movement of the elution liquid back and forth (in the directions F8 and F9) is carried out by pushing it (in the direction F10) and by releasing (in the direction F11) through the third control element (32) at least once from the second chamber (6) towards or into the first chamber (5) by compression of the air trapped in the first chamber (5), the first and second control elements (12 and 22) being closed, wherein the nucleic acids are released into the elution liquid, while being incubated between 35 and 50° C., preferably at substantially 40° C., the support (3) is translated relative to the drawer (4) into a fourth translatory position, and the liquid is incubated by keeping the first, second and third control means (12, 22 and 32) closed and by incubating the second chamber (6) between 40 and 80° C., preferably at substantially 65° C., which makes possible the hybridisation of the nucleic acids on the reaction chip (29), the second chamber (6) is washed and an optical reading of the hybridisation of the nucleic acids on the reaction chip (29) is carried out.

\* \* \* \* \*